(12) United States Patent
Minai et al.

(10) Patent No.: US 10,979,922 B2
(45) Date of Patent: Apr. 13, 2021

(54) ESTIMATION DEVICE, MEDICAL SYSTEM, AND ESTIMATION METHOD

(71) Applicant: OLYMPUS CORPORATION, Tokyo (JP)

(72) Inventors: Tetsuo Minai, Hachioji (JP); Takeshi Nishiyama, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/846,510

(22) Filed: Apr. 13, 2020

(65) Prior Publication Data

US 2020/0245170 A1 Jul. 30, 2020

Related U.S. Application Data

(63) Continuation of application No. PCT/JP2018/028407, filed on Jul. 30, 2018.

(30) Foreign Application Priority Data

Oct. 19, 2017 (JP) .............................. JP2017-202750

(51) Int. Cl.
*H04N 7/18* (2006.01)
*H04W 24/08* (2009.01)
(Continued)

(52) U.S. Cl.
CPC ......... *H04W 24/08* (2013.01); *A61B 1/00006* (2013.01); *A61B 1/00009* (2013.01);
(Continued)

(58) Field of Classification Search
CPC ..... H04W 24/08; H04W 28/04; H04W 24/04; A61B 1/00006; A61B 1/00009;
(Continued)

(56) References Cited

U.S. PATENT DOCUMENTS 9,011,329 B2 * 4/2015 Ferren .............. A61B 17/22012
600/309
10,785,428 B2 * 9/2020 Wang ....................... A61B 1/06
(Continued)

FOREIGN PATENT DOCUMENTS

JP H05-176019 A 7/1993
JP 2012-040414 A 3/2012
(Continued)

OTHER PUBLICATIONS

Itoh et al, A 2.6mW 2 fps QVGA CMOS one-chip wireless camera with digital image transmission function for capsule endoscope (Year: 2006).*

(Continued)

*Primary Examiner* — Shan E Elahi
(74) *Attorney, Agent, or Firm* — Scully, Scott, Murphy & Presser, P.C.

(57) ABSTRACT

An estimation device includes a processor configured to: detect an error of data obtained by receiving a wireless signal from a medical device; correct the detected error; determine whether or not there is a noise due to an external generation source at a time of acquiring the wireless signal from the medical device, based on detection information relevant to the detected error or correction information relevant to the corrected error; and estimate a cause of the noise, based on the detection information or the correction information. The detection information is at least one of the number of detections of the error, continuousness of the error, and periodicity of the error, and the correction information is at least one of the number of corrections of the error, continuousness of data in which the error is corrected, and periodicity of data in which the error is corrected.

16 Claims, 11 Drawing Sheets

(51) Int. Cl.
  *A61B 1/00* (2006.01)
  *A61B 1/04* (2006.01)
  *H04N 5/225* (2006.01)
  *H04W 28/04* (2009.01)

(52) U.S. Cl.
  CPC .......... *A61B 1/00016* (2013.01); *A61B 1/041* (2013.01); *H04N 5/2256* (2013.01); *H04W 28/04* (2013.01); *H04N 2005/2255* (2013.01)

(58) Field of Classification Search
  CPC . A61B 1/00016; A61B 1/041; A61B 1/00057; H04N 5/2256; H04N 2005/2255; H04L 1/00; G02B 23/24
  USPC .......................................................... 348/45
  See application file for complete search history.

(56) References Cited

U.S. PATENT DOCUMENTS

| | | | |
|---|---|---|---|
| 2013/0172671 A1* | 7/2013 | Rentschler | ............. A61B 1/041 600/109 |
| 2015/0105619 A1 | 4/2015 | Luiken | |
| 2016/0174809 A1* | 6/2016 | Wang | .................... A61B 1/0002 600/109 |
| 2016/0249793 A1* | 9/2016 | Wang | ....................... A61B 1/31 600/109 |
| 2017/0078901 A1 | 3/2017 | Iwanaga et al. | |
| 2017/0119278 A1 | 5/2017 | Hyde et al. | |
| 2017/0185056 A1 | 6/2017 | Satou | |
| 2018/0213207 A1* | 7/2018 | Wilson | ................. H04N 5/2259 |

FOREIGN PATENT DOCUMENTS

| | | |
|---|---|---|
| JP | 2016-149722 A | 8/2016 |
| JP | 2017-117180 A | 6/2017 |
| WO | WO 2015/182752 A1 | 12/2015 |

OTHER PUBLICATIONS

International Search Report dated Oct. 2, 2018 issued in PCT/JP2018/028407.

* cited by examiner

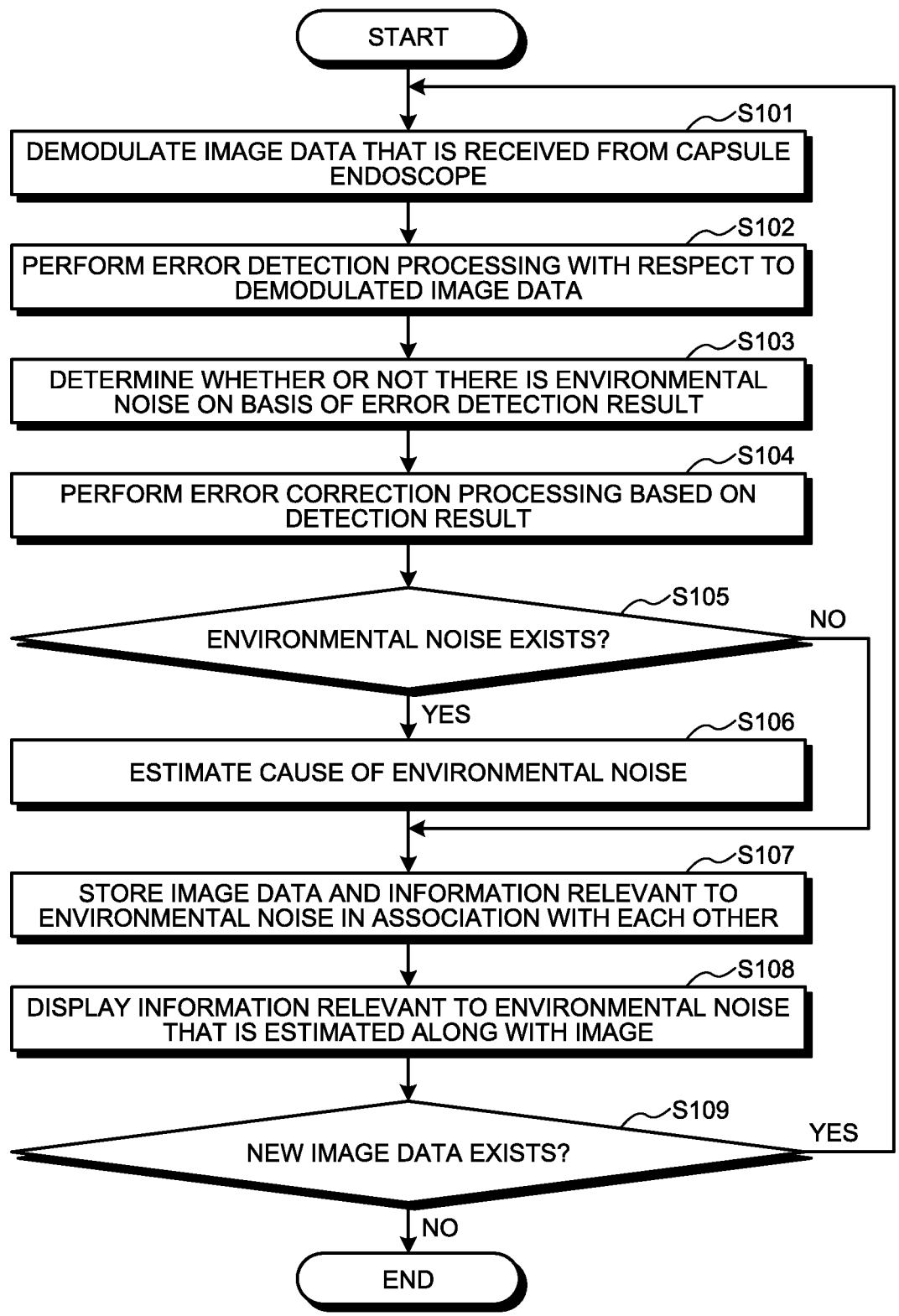

FIG.4

| CHARACTERISTICS OF DATA IN WHICH ERROR IS DETECTED | | | | | CAUSE CANDIDATE OF ENVIRONMENTAL NOISE |
|---|---|---|---|---|---|
| NUMBER OF PIECES (NUMBER OF DATA ITEMS) | CONTIN-UOUSNESS (NUMBER OF DATA ITEMS) | PERIODICITY 1 (NUMBER OF DATA ITEMS) | PERIODICITY 2 (NUMBER OF LINES) | NUMBER OF FRAMES AT TIME OF DETERMINATION | |
| - | 50 TO 100 | - | 5 TO 7 | 10 | EXTERNAL DEVICE 1 |
| - | 50 TO 100 | - | 10 TO 12 | 10 | EXTERNAL DEVICE 2 |
| - | 100 TO 1000 | - | 3 TO 5 | 5 | EXTERNAL DEVICE 3 |
| 100 TO 200 | 1 TO 10 | 1000 TO 2000 | - | 5 | EXTERNAL DEVICE 4 |
| 200 TO 400 | 1 TO 10 | 6000 TO 7000 | - | 5 | EXTERNAL DEVICE 5 |
| - | 500 TO 1000 | - | 50 TO 100 | 20 | EXTERNAL WIRE-LESS COMMUNI-CATION 1 |
| 500 TO 1000 | 100 TO 1000 | - | 100 TO 300 | 20 | EXTERNAL WIRE-LESS COMMUNI-CATION 2 |
| 500 TO 1000 | - | 5 TO 10 | - | 3 | EXTERNAL WIRE-LESS COMMUNI-CATION 3 |
| 500 TO 1000 | - | 50 TO 60 | - | 3 | EXTERNAL WIRE-LESS COMMUNI-CATION 4 |

FIG.5

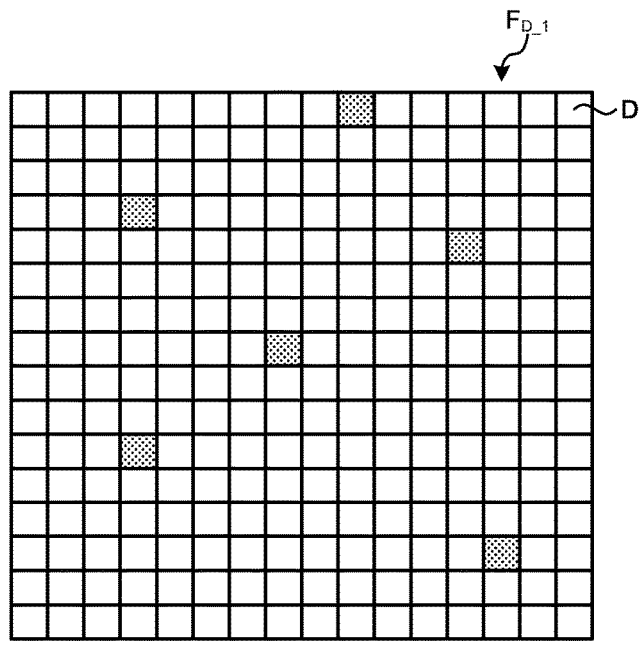

ESTIMATION DEVICE, MEDICAL SYSTEM, AND ESTIMATION METHOD

CROSS-REFERENCE TO RELATED APPLICATION

This application is a continuation of PCT International Application No. PCT/JP2018/028407 filed on Jul. 30, 2018, which designates the United States, incorporated herein by reference, and which claims the benefit of priority from Japanese Patent Application No. 2017-202750, filed on Oct. 19, 2017, incorporated herein by reference.

BACKGROUND

1. Technical Field

The present disclosure relates to an estimation device that performs image processing with respect to image data, a medical system, and an estimation method.

2. Related Art

In the related art, an endoscope is widely used as a medical observation apparatus that is inserted into the body of a subject such as a patient and observes the inside of the subject. In addition, recently, a capsule endoscope that is a swallow type image acquiring device provided with an imaging device and a communication device wirelessly transmitting, to the outside of the body, image data that is captured by the imaging device in a capsule-shaped casing has been developed. The capsule endoscope, for example, is moved in an internal organ such as esophagus, stomach, and small intestine, in accordance with the peristaltic motion, and sequentially performs capturing, after being swallowed from the mouth of the patient for observing the inside of the subject and before being spontaneously excreted from the subject.

The image data that is captured by the capsule endoscope while being moved in the subject is sequentially transmitted to the outside of the body by wireless communication, and is accumulated in a memory that is provided inside or outside a receiving device on the outside of the body. A medical doctor or a nurse takes the image data that is accumulated in the memory in an image processing device through a cradle into which the receiving device is inserted, and thus, is capable of performing diagnosis, on the basis of an image that is displayed on a display of the image processing device.

Predicting the occurrence of a communication failure in the wireless communication is important for generating an accurate image and for performing suitable diagnosis. For example, in WO 2015/182752 A, the occurrence of the communication failure is predicted by comparing an image that is captured with a reference image.

SUMMARY

In some embodiments, an estimation device includes a processor including hardware, the processor being configured to: detect an error of data obtained by receiving a wireless signal from a medical device configured to be inserted into a subject; correct the detected error; determine whether or not there is a noise due to an external generation source at a time of acquiring the wireless signal from the medical device, based on detection information relevant to the detected error or correction information relevant to the corrected error; and estimate a cause of the noise, based on the detection information or the correction information, when it is determined that there is the noise. The detection information is at least one of the number of detections of the error, continuousness of the error, and periodicity of the error, and the correction information is at least one of the number of corrections of the error, continuousness of data in which the error is corrected, and periodicity of data in which the error is corrected.

In some embodiments, a medical system includes: a medical device to be inserted into a subject, the medical device being configured to output a wireless signal; a receiver configured to receive the wireless signal; a first processor comprising hardware, the first processor being connected to the receiver to communicate with the receiver; and a display. The receiver includes a second processor comprising hardware, and a position information receiver configured to acquire position information of the receiver. The second processor is configured to detect an error of data obtained by receiving the wireless signal from the medical device, correct the detected error, determine whether or not there is a noise due to an external generation source at a time of acquiring the wireless signal from the medical device, based on detection information relevant to the detected error or correction information relevant to the corrected error, and estimate a cause of the noise, based on the detection information or the correction information, when it is determined that there is the noise. The detection information is at least one of the number of detections of the error, continuousness of the error, and periodicity of the error. The correction information is at least one of the number of corrections of the error, continuousness of the data in which the error is corrected, and periodicity of the data in which the error is corrected. The first processor is configured to cause the display to display information in which the position information and the cause of the noise are associated with each other on the display.

In some embodiments, provided is an estimation method performed by an estimation device configured to estimate a cause of a noise due to an external generation source, based on data obtained by receiving a wireless signal from a medical device configured to be inserted into a subject. The method includes: detecting an error of the data; correcting the detected error; determining whether or not there is the noise at a time of acquiring the wireless signal from the medical device, based on detection information relevant to the detected error or correction information relevant to the corrected error; and estimating the cause of the noise, based on the detection information or the correction information, when it is determined that there is the noise. The detection information is at least one of the number of detections of the error, continuousness of the error, and periodicity of the error, and the correction information is at least one of the number of corrections of the error, continuousness of the data in which the error is corrected, and periodicity of the data in which the error is corrected.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 3 is a flowchart illustrating environmental noise estimation processing that is performed by the capsule endoscope system according to the first embodiment of the disclosure;

FIG. 4 is a diagram describing a cause estimation table of an environmental noise in the environmental noise estimation processing that is performed by the capsule endoscope system according to the first embodiment of the disclosure;

FIG. 5 is a diagram describing a relationship between an error detection position on an image and an environmental noise to be estimated;

DETAILED DESCRIPTION

Figure 1:
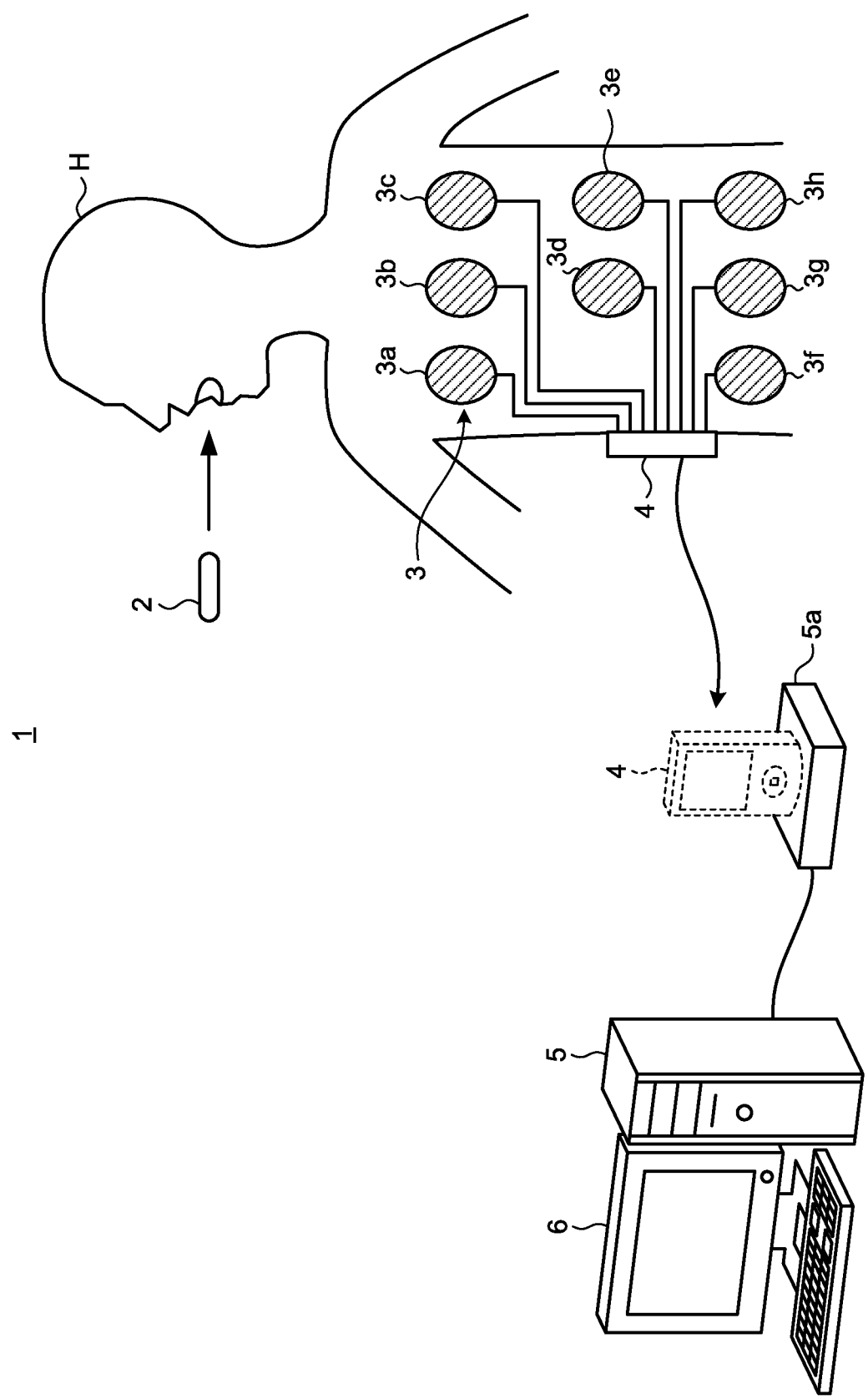
FIG. 1 is a schematic view illustrating a schematic configuration of a capsule endoscope system according to a first embodiment of the disclosure.

Hereinafter, a capsule endoscope system in which an estimation device is provided and a medical capsule endoscope is used will be described as an embodiment of the disclosure. Note that, in the description of the drawings, the same reference numerals are applied to the same portions. In addition, it is necessary to note that the drawings are schematic, and a relationship between the thickness and the width of each member, a ratio of each member, and the like are different from the actuals.

First Embodiment

FIG. 1 is a schematic view illustrating a schematic configuration of a capsule endoscope system according to a first embodiment of the disclosure. As illustrated in FIG. 1, a capsule endoscope system 1 according to the first embodiment includes a capsule endoscope 2 that is a medical device that is inserted into a subject H, generates image data by capturing the inside of the subject H, and transmits the image data superimposed on a wireless signal through an electric wave, a receiving device 4 that receives the wireless signal transmitted from the capsule endoscope 2 through a receiving antenna unit 3 including a plurality of receiving antennas 3a to 3h mounted on the subject H, and a processing device 5 that takes the image data generated by the capsule endoscope 2 from the receiving device 4 through a cradle 5a, processes the image data, and generates an in-vivo image of the subject H. The image that is generated by the processing device 5, for example, is displayed and output from a display device 6. Herein, in the image that is generated by the capsule endoscope 2, an image in a state of being converted into a transmission format for transmission to the processing device 5 from the capsule endoscope 2 is referred to as the image data.

The capsule endoscope 2 is swallowed by the subject H, and then, sequentially captures a biological portion (the esophagus, the stomach, the small intestine, the large intestine, and the like) during a reference period set in advance (for example, a period of 0.5 seconds) while being moved in the digestive canal of the subject H by the peristaltic motion or the like of the internal organ. Then, the image data that is acquired by the imaging operation and associated information are sequentially transmitted wirelessly to the receiving device 4.

Figure 2:
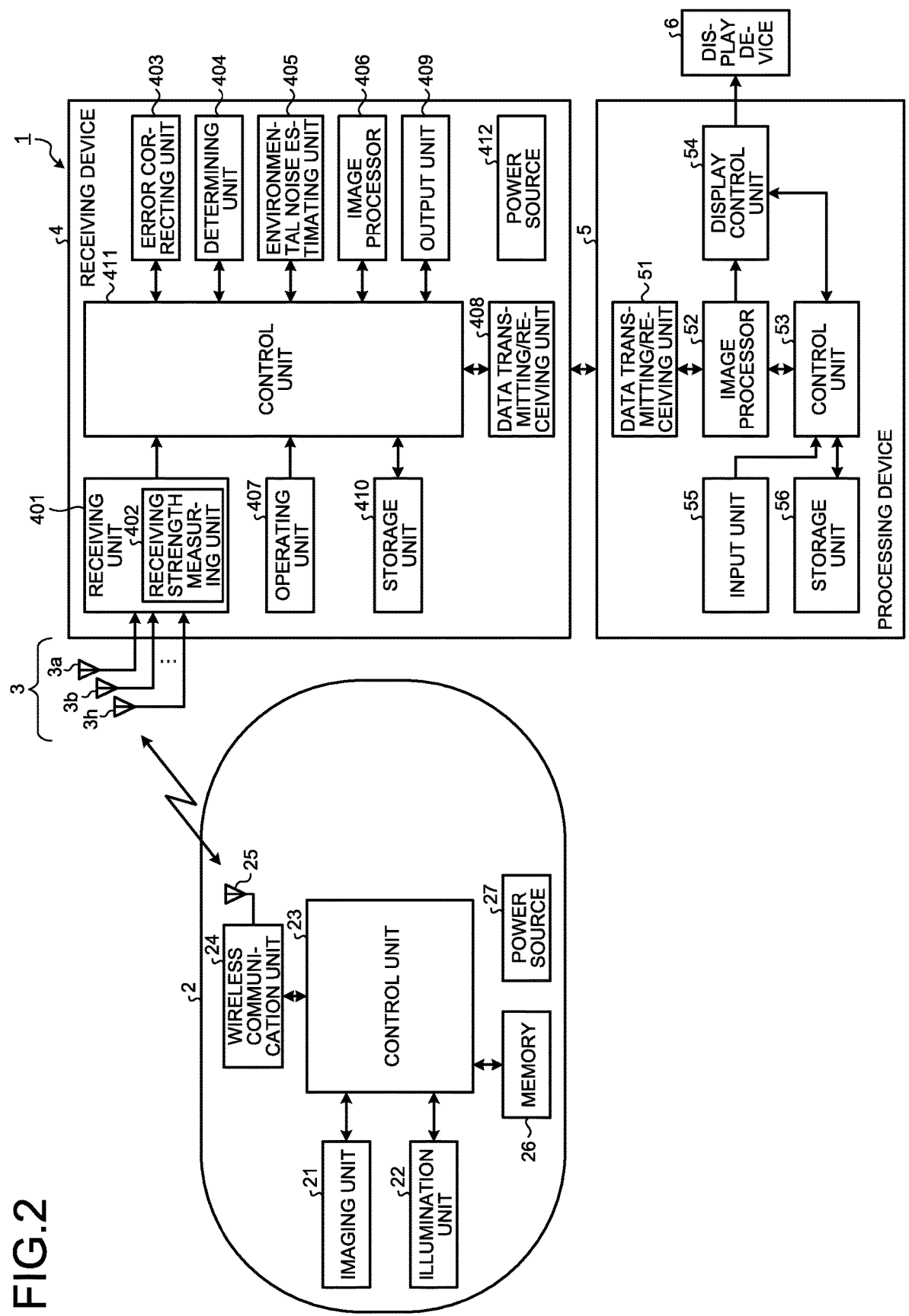
FIG. 2 is a block diagram illustrating the schematic configuration of the capsule endoscope system according to the first embodiment of the disclosure.

FIG. 2 is a block diagram illustrating the schematic configuration of the capsule endoscope system according to the first embodiment of the disclosure. The capsule endoscope 2 includes an imaging unit 21, an illumination unit 22, a control unit 23, a wireless communication unit 24, an antenna 25, a memory 26, and a power source 27. The capsule endoscope 2 is a device in which each constituent described above is built in a capsule-shaped casing having a size that can be swallowed by the subject H.

The imaging unit 21, for example, includes an image sensor that generates and outputs the image data obtained by capturing the inside of the subject H from an optical image formed on a light receiving surface, and an optical system such as an objective lens that is disposed on the light receiving surface side of the image sensor. The image sensor includes a charge coupled device (CCD) image sensor or a complementary metal oxide semiconductor (CMOS) image sensor, includes a plurality of pixels that receive light from the subject H and are arranged into the shape of a matrix, and performs photoelectric conversion with respect to the light received by the pixels, and thus, generates the image data. The imaging unit 21 reads out a pixel value for each horizontal line, with respect to the plurality of pixels that are arranged into the shape of a matrix, and generates the image data including a plurality of line data items to which a synchronization signal is applied for each of the horizontal lines.

The illumination unit 22 includes a white LED that generates white light that is illumination light, and the like. Note that, the white light may be generated by multiplexing light having different outgoing wavelength bands of a plurality of LEDs, a laser light source, or the like in addition to the white LED, or may be configured by using a xenon lamp, a halogen lamp, and the like.

The control unit 23 controls operation processing of each of the constituents of the capsule endoscope 2. For example, in a case where the imaging unit 21 performs imaging processing, the imaging unit 21 is controlled such that exposure and readout processing are executed with respect to the image sensor, and the illumination unit 22 is controlled such that the illumination light is emitted in accordance with an exposure timing of the imaging unit 21. In addition, the control unit 23 determines a light emitting time of the illumination unit 22 at the time of performing the next capturing, from a pixel value (a luminance value) of the image data captured by the imaging unit 21, and controls the illumination unit 22 such that the illumination light is emitted at the determined light emitting time. As described above, there is a case where the light emitting time of the illumination unit 22 is controlled on the basis of the image data captured by the control unit 23, and the light emitting time is changed every time when the capturing is performed. The control unit 23 is configured by using a general-purpose processor such as a central processing unit (CPU), or a dedicated processor such as various arithmetic circuits executing a specific function, such as an application specific integrated circuit (ASIC).

The wireless communication unit 24 performs modulation processing with respect to the image data that is output from the imaging unit 21, and transmits the image data to the outside. The wireless communication unit 24 performs A/D conversion and predetermined signal processing with respect to the image data that is output from the imaging unit 21, acquires the image data in a digital format, superimposes the image data on the wireless signal along with the associated information, and transmits the image data to the outside from the antenna 25. The associated information includes identification information (for example, a serial number) allocated in order to identify the individual capsule endoscope 2, and the like.

The memory 26 stores an execution program and a control program for the control unit 23 to execute various operations, and a parameter such as a threshold value. In addition, the memory 26 may temporarily store the image data or the like that is subjected to the signal processing in the wireless communication unit 24. The memory 26 includes a random access memory (RAM), a read only memory (ROM), and the like.

The power source 27 includes a battery including a button battery or the like, a power circuit supplying power to each unit, and a power switch switching an On/Off state of the power source 27, and supplies the power to each unit in the capsule endoscope 2 after the power switch is turned on. Note that, the power switch, for example, includes a reed switch of which an On/Off state is switched in accordance with an external magnetic force, and is switched to an On state by applying the magnetic force to the capsule endoscope 2 from the outside, before the capsule endoscope 2 is used (before the capsule endoscope 2 is swallowed by the subject H).

The receiving device 4 includes a receiving unit 401, a receiving strength measuring unit 402, an error correcting unit 403, a determining unit 404, an environmental noise estimating unit 405, an image processor 406, an operating unit 407, a data transmitting/receiving unit 408, an output unit 409, a storage unit 410, a control unit 411, and a power source 412 supplying power to each of the units.

The receiving unit 401 receives the wireless signal that is wirelessly transmitted from the capsule endoscope 2. Specifically, the image data and the associated information that are wirelessly transmitted from the capsule endoscope 2 are received through the receiving antenna unit 3 including the plurality of (in FIG. 1, eight) receiving antennas 3a to 3h. The receiving antennas 3a to 3h, for example, are attained by using a loop antenna or a dipole antenna, and are disposed in a predetermined position on the surface of the outside of the subject H. The receiving unit 401 includes the receiving strength measuring unit 402 that measures a receiving strength of the wireless signal received by the receiving antennas 3a to 3h (received signal strength indicator (RSSI)). The receiving unit 401 selects an antenna having the highest receiving strength in the receiving antennas 3a to 3h, on the basis of the receiving strength measured by the receiving strength measuring unit 402, and receives the wireless signal that is received by the selected antenna. In addition, the receiving unit 401, for example, includes a processor such as a CPU or an ASIC, and performs the predetermined signal processing such as demodulation processing or the A/D conversion, with respect to the received image data.

The receiving strength measuring unit 402 measures the receiving strength when the receiving unit 401 receives the wireless signal, with respect to each of the receiving antennas 3a to 3h. At this time, all of the measured receiving strengths and the image data received by the receiving unit 401 may be associated with each other, and may be stored in the storage unit 410.

The error correcting unit 403 detects an error of the image data that is received by the receiving unit 401, and corrects the detected error. Specifically, the error correcting unit 403 performs error detection by using one pixel unit or a plurality of pixels set in advance as one detection unit. Examples of an error detection method include a known method, for example, a method using redundancy. The error correcting unit 403 outputs a detection result to the control unit 411, along with the image data after being corrected. In addition, the error correcting unit 403 performs correction processing by using a known method such as interpolation processing based on surrounding pixel values. The error correcting unit 403 is attained by a processor such as a CPU or an ASIC.

The determining unit 404 determines whether or not an environmental noise is superimposed on the image data, on the basis of the number of detections of the error that is detected by the error correcting unit 403 or a detection pattern. Here, the environmental noise is a noise that is generated by the operation of an external wireless transmission source that is different from the capsule endoscope 2 or the receiving device 4, such as an automatic door or keyless entry of an automobile, and is a noise due to the external circumstances, but not an immanent noise of the subject H. The determining unit 404 is attained by a processor such as a CPU or an ASIC.

The environmental noise estimating unit 405 estimates the cause of the superimposed environmental noise, with respect to the image data that is determined by the determining unit 404 that the environmental noise is superimposed on the image data. The environmental noise estimating unit 405 is attained by a processor such as a CPU or an ASIC. Estimation processing of the environmental noise estimating unit 405 will be described below.

The image processor 406 performs the predetermined image processing for preparing an in-vivo image corresponding to the image data that is received by the receiving unit 401 or the image data that is stored in the storage unit 410 by reading a predetermined program stored in the storage unit 410. The image processor 406 is attained by a processor such as a CPU or an ASIC.

The operating unit 407 is an input device that is used when a user inputs various setting information items or instruction information items into the receiving device 4. The operating unit 407, for example, is a switch, a button, or the like that is provided on a manipulation panel of the receiving device 4.

The data transmitting/receiving unit 408 transmits the image data and the associated information that are stored in the storage unit 410 to the processing device 5 at the time of being connected to the processing device 5 in a state where communication can be performed. The data transmitting/receiving unit 408 includes a communication interface such as a LAN.

The output unit 409 displays an image, outputs a sound or light, and generates a vibration. The output unit 409 displays the image that is generated by the image processor 406, or emits the sound, the light, and the vibration. The output unit 409 includes at least one of a display such as a liquid crystal display and an organic EL display, a speaker, a light source such as an LED, and a vibration generator such as a vibration motor. In the first embodiment, the output unit 409 includes the display and the speaker.

The storage unit 410 stores a program for executing various functions by operating the receiving device 4, the image data that is acquired by the capsule endoscope 2, or the like. The storage unit 410 includes a RAM, a ROM, and the like.

The control unit 411 controls each constituent of the receiving device 4. The control unit 411 is configured by using a general-purpose processor such as a CPU, and a dedicated processor such as various arithmetic circuits executing a specific function, such as an ASIC.

Such a receiving device 4 is carried by being mounted on the subject H while the capturing is performed by the capsule endoscope 2, for example, until the capsule endoscope 2 passes through the digestive canal and is excreted after being swallowed by the subject H. The receiving device 4 stores the image data that is received through the receiving antenna unit 3 in the storage unit 410, during such a period.

The receiving device 4 is removed from the subject H after the capturing of the capsule endoscope 2 is ended, and is set in the cradle 5a that is connected to the processing device 5 (refer to FIG. 1). Accordingly, the receiving device 4 is connected to the processing device 5 in a state where communication can be performed, and transmits (downloads) the image data and the associated information that are stored in the storage unit 410 to the processing device 5.

The processing device 5, for example, is configured by using a workstation provided with the display device 6 such as a liquid crystal display. The processing device 5 includes a data transmitting/receiving unit 51, an image processor 52, a control unit 53 that totally controls each unit, a display control unit 54, an input unit 55, and a storage unit 56.

The data transmitting/receiving unit 51 is an interface that can be connected to a USB, or a communication line such as a wired LAN or a wireless LAN, and includes a USB port and a LAN port. In the first embodiment, the data transmitting/receiving unit 51 is connected to the receiving device 4 through the cradle 5a that is connected to the USB port, and transmits and receives data with respect to the receiving device 4.

The image processor 52 performs the predetermined image processing for preparing the in-vivo image corresponding to the image data input from the data transmitting/receiving unit 51 or the image data stored in the storage unit 56, by reading a predetermined program that is stored in the storage unit 56 described below. The image processor 52 is attained by a processor such as a CPU or an ASIC.

The control unit 53 performs the transmission of an instruction, data, or the like with respect to each unit configuring the processing device 5, on the basis of the signal that is input through the input unit 55 or the image data that is input from the data transmitting/receiving unit 51, by reading various programs that are stored in the storage unit 56, and totally controls the entire operation of the processing device 5. The control unit 53 is attained by a general-purpose processor such as a CPU, or a dedicated processor such as various arithmetic circuits executing a specific function, such as an ASIC.

The display control unit 54 performs predetermined processing such as data decimation or gradation processing according to a display range of an image in the display device 6, with respect to the image that is generated in the image processor 52, and then, displays and outputs the image onto the display device 6. The display control unit 54, for example, includes a processor such as a CPU, an ASIC, or the like.

The input unit 55 receives the input of information or a command according to the manipulation of the user. The input unit 55, for example, is attained by an input device such as a keyboard or a mouse, a touch panel, and various switches.

The storage unit 56 stores a program for executing various functions by operating the processing device 5, various information items that are used in the execution of the program, and the image data and the associated information that are acquired through the receiving device 4, the in-vivo image that is prepared by the image processor 52, and the like. The storage unit 56 is attained by a semiconductor memory such as a flash memory, a RAM, and a ROM, a recording medium such as an HDD, MO, a CD-R, and a DVD-R, a driving device driving the recording medium, and the like.

Subsequently, environmental noise estimation processing that is executed by the receiving device 4 will be described. FIG. 3 is a flowchart illustrating the environmental noise estimation processing that is performed by the capsule endoscope system according to the first embodiment of the disclosure. Hereinafter, it will be described that each unit is operated under the control of the control unit 411.

The receiving unit 401 demodulates the image data that is received from the capsule endoscope 2 (Step S101).

In Step S102 subsequent to Step S101, the error correcting unit 403 performs the error detection with respect to the image data after the demodulation processing (a detection step).

In Step S103 subsequent to Step S102, the error correcting unit 403 performs error correction processing with respect to the image data, on the basis of an error detection result of Step S102 (a correction step).

In Step S104 subsequent to Step S103, the determining unit 404 determines whether or not there is the environmental noise of the image data, on the basis of the error detection result of the error correcting unit 403.

FIG. 4 is a diagram describing a cause estimation table of the environmental noise in the environmental noise estimation processing that is performed by the capsule endoscope system according to the first embodiment of the disclosure. In the first embodiment, the cause estimation table illustrated in FIG. 4 is stored in the storage unit 410. In a case where a pixel value of each pixel position is set as one data item, and a horizontal line of a pixel sequentially follows data in a vertical direction along a predetermined direction, the cause estimation table indicates a relationship between the number of detections of the error (the number of data items), the continuousness of the error (the number of consecutive data items), periodicity (the number of data items or the number of lines), and the number of frames required for determination, and a cause candidate of the environmental noise. As described above, in the cause estimation table, at least one of the number of detections of the error, the continuousness, the periodicity, and the number of frames, and the external generation source (the cause)

generating the environmental noise are associated with each other. Examples of external devices 1 to 5 include a medical telemeter, a cathode-ray tube monitor, automobile keyless entry, toys, a transceiver, and the like. Examples of external wireless communications 1 to 4 include a crime prevention system, a waitress call system, an automatic door, a garage opener, and the like.

In Step S104, in a case where the determining unit 404 determines that there is the environmental noise, on the basis of the number of detections of the error, the continuousness, the periodicity, with reference to the cause estimation table as described above (Step S105: Yes), the control unit 411 proceeds to Step S106. In contrast, in a case where the determining unit 404 determines that there is no environmental noise (Step S105: No), the control unit 411 proceeds to Step S107.

Figure 6:
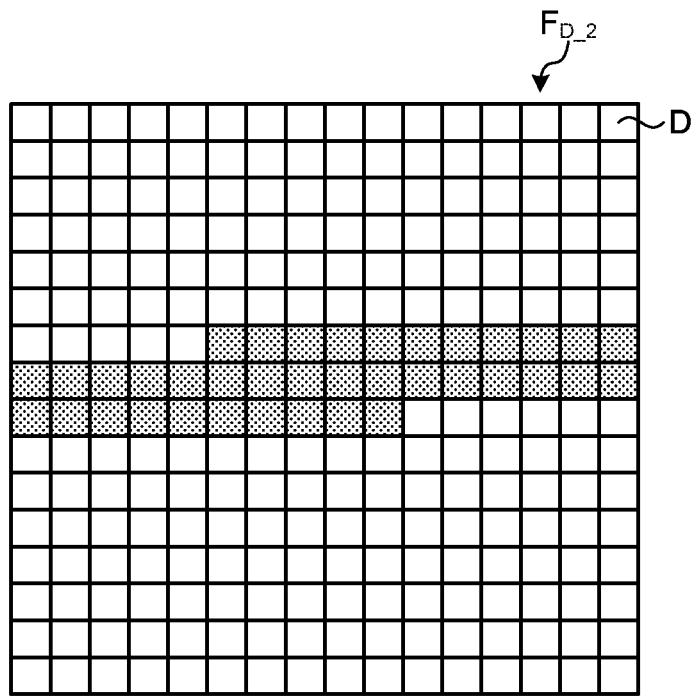
FIG. 6 is a diagram describing a relationship between the error detection position on the image and the environmental noise to be estimated.
Figure 7:
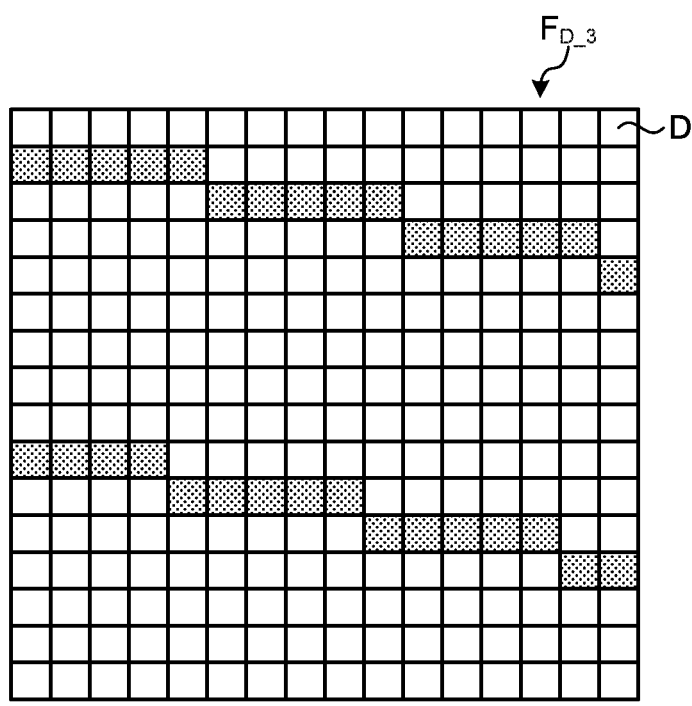
FIG. 7 is a diagram describing a relationship between the error detection position on the image and the environmental noise to be estimated.

In Step S106, the environmental noise estimating unit 405 estimates the cause of the environmental noise, on the basis of the cause estimation table described above. FIGS. 5 to 7 are diagrams describing a relationship between an error detection position on the image and the environmental noise to be estimated. For example, in a case where 5 to 10 data items in which an error is detected appear in three frames in a determination target range, and the total is 600, the environmental noise estimating unit 405 estimates that there is the environmental noise and the cause thereof is the external wireless communication 3. In this case, for example, as with image data $F_{D\_1}$ illustrated in FIG. 5, data D in which an error is detected (data D represented by hatching), in each of data items D configuring the image data $F_{D\_1}$, is in a state of being dotted.

In addition, in a case where the data items in which the error is detected are consecutive along the horizontal line direction (refer to FIG. 6), the environmental noise estimating unit 405 estimates the cause of the environmental noise, in accordance with the continuousness or the periodicity, and the number of frames at the time of the determination. For example, in a case where 600 data items in which the error is detected are consecutive and appear for each of 70 lines, in 20 frames in the determination target range, the environmental noise estimating unit 405 estimates that there is the environmental noise and the cause thereof is the external wireless communication 1. In this case, for example, as with image data $F_{D\_2}$ illustrated in FIG. 6, the data D in which the error is detected (the data D represented by hatching), in each of data items D configuring the image data $F_{D\_2}$, is in a state of being consecutive along the line.

In addition, in a case where the data in which the error is detected is repeated in a predetermined pattern, along the horizontal line direction (refer to FIG. 7), the environmental noise estimating unit 405 estimates the cause of the environmental noise, in accordance with the continuousness or the periodicity, and the number of frames at the time of the determination. For example, in a case where a pattern in which 60 data items in which the error is detected are consecutive appears for each of 7 lines, in ten frames in the determination target range, the environmental noise estimating unit 405 estimates that there is the environmental noise and the cause thereof is the external device 1. In this case, for example, as with image data $F_{D\_3}$ illustrated in FIG. 7, the data D in which the error is detected (the data D represented by hatching), in each of data items D configuring the image data $F_{D\_3}$, repeats a predetermined pattern.

In Step S107, the control unit 411 associates the image data and information relevant to the environmental noise, such as the determination result or the estimation result, with each other, and stores the image data and the information relevant to the environmental noise in the storage unit 410. At this time, for example, in a case where it is determined that there is no environmental noise, the image data and information to the effect that there is no environmental noise are associated with each other. In contrast, in a case where it is determined that there is the environmental noise, the image data, information to the effect that there is the environmental noise, and the estimated cause are associated with each other.

Figure 8:
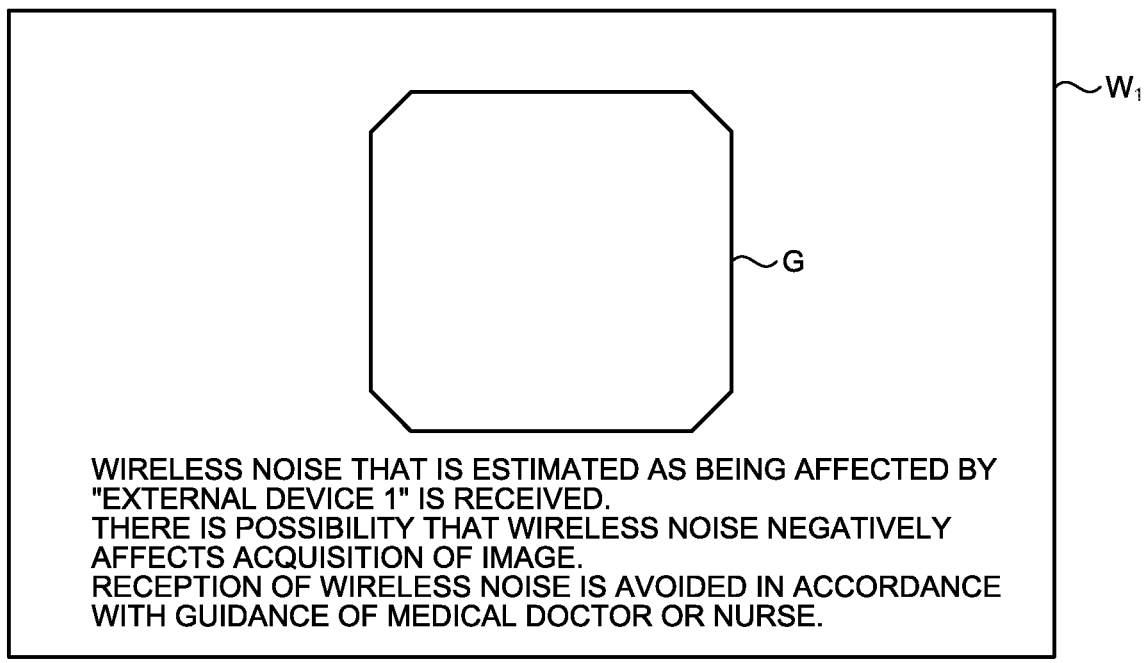
FIG. 8 is a diagram illustrating an example of display of information relevant to an estimated environmental noise, in the capsule endoscope system according to the first embodiment of the disclosure.

In Step S108 subsequent to Step S107, the control unit 411 causes the output unit 409 (the display) to display the information relevant to the environmental noise on the output unit 409, along the image corresponding to the image data. FIG. 8 is a diagram illustrating an example of the display of information relevant to the estimated environmental noise, in the capsule endoscope system according to the first embodiment of the disclosure. In Step S108, for example, as with a screen $W_1$ illustrated in FIG. 8, in a case where the image corresponding to the image data is displayed in an image display area G, and there is the estimation result of the environmental noise, the cause to be estimated, and a guide for the subject to avoid the environmental noise are displayed under the image display area G.

When the image is displayed on the display, the output unit 409 notifies that the image is displayed on the display by emitting a sound. Note that, in a case where there is at least the environmental noise, it is preferable that output processing in Step S108 is executed within a predetermined time after the estimation processing of the environmental noise has been ended, for example, within several seconds. The control unit 411 performs notification with respect to the output unit 409, preferably within 3 seconds, more preferably within 2 seconds, and even more preferably within 1 second, after the estimation processing has been ended.

The user mounted with the receiving device 4 checks the image that is displayed on the display (refer to FIG. 8), and thus, it is possible to avoid the environmental noise and to suppress the noise that is superimposed on the image data.

After that, the control unit 411 determines whether or not new image data is received (Step S109). In a case where the control unit 411 determines that new image data is received (Step S109: Yes), the control unit 411 returns to Step S101, and the processing described above is repeated with respect to the image data that is newly received. In contrast, in a case where the new image data is not received (Step S109: No), the control unit 411 ends the environmental noise estimation processing.

In the first embodiment described above, it is determined whether or not there is the environmental noise, on the basis of the detection information of the error in the image data (specifically, the number of detections or the error, and the continuousness or the periodicity of the detected data), and in a case where there is the environmental noise, the cause of the environmental noise is estimated. According to the first embodiment, it is possible to estimate the wireless transmission source (the cause) that should be avoided in order to suppress the noise superimposed on the image data.

Note that, in the first embodiment described above, the error correcting unit 403 estimates the presence or absence of the environmental noise or the cause by using the number of detections of the detected error data, but the presence or absence of the environmental noise or the cause may be estimated on the basis of correction information relevant to the error correction that is performed by the error correcting unit 403 (specifically, the number of corrections, and the continuousness or the periodicity of the corrected data).

In addition, in the first embodiment described above, it has been described that the cause estimation table illustrated in FIG. 4 is stored in advance in the storage unit 410, but the determining unit 404 or the environmental noise estimating unit 405 may acquire the cause estimation table from the outside through a network.

First Modification Example of First Embodiment

Figure 9:
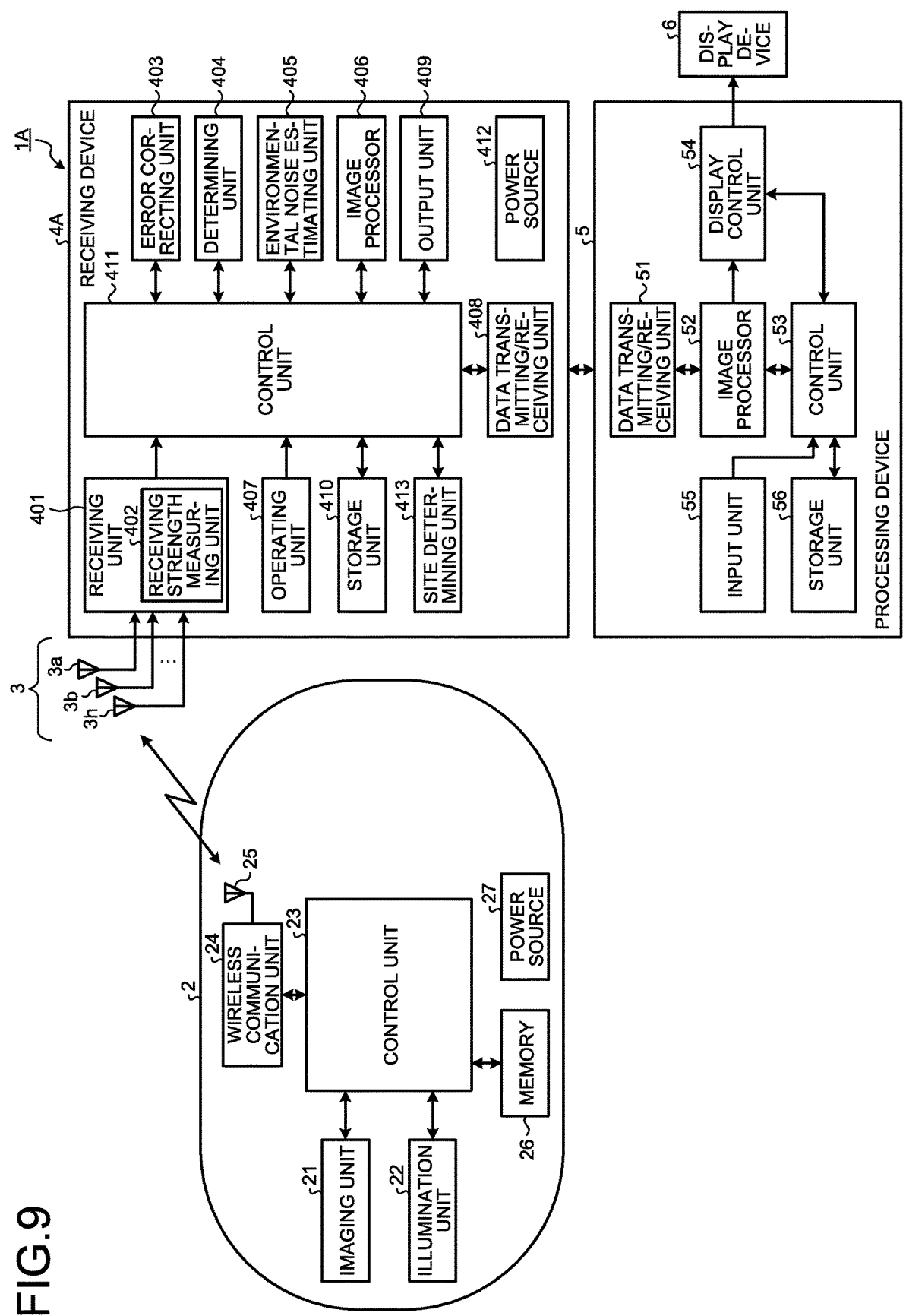
FIG. 9 is a block diagram illustrating a schematic configuration of a capsule endoscope system according to a first modification example of the first embodiment of the disclosure.

Subsequently, a first modification example of the first embodiment of the disclosure will be described. FIG. 9 is a diagram illustrating the configuration of a capsule endoscope provided in a capsule endoscope system according to the first modification example of the first embodiment of the disclosure. A capsule endoscope system 1A according to the first modification example is different from the capsule endoscope system 1 described above in that a receiving device 4A is provided instead of the receiving device 4. The other configurations are identical to those of the capsule endoscope system 1. Hereinafter, a configuration and processing different from that of the first embodiment described above will be described with reference to FIG. 9.

The receiving device 4A further includes a site determining unit 413, in addition to the configuration of the receiving device 4 described above. The site determining unit 413 acquires the receiving strength of each of the receiving antennas 3a to 3h, and determines a site of the subject in which the capsule endoscope 2 exists, on the basis of the size of the receiving strength. The site determining unit 413 determines the site in which the capsule endoscope 2 exists, along with the size of the receiving strength of each of the receiving antennas 3a to 3h (a strength distribution), and the information that is stored in the storage unit 410. At this time, a relationship table of the strength distribution of the receiving strengths of the receiving antennas 3a to 3h and the site of the subject corresponding to the position thereof is stored in the storage unit 410. Further, the cause estimation table for estimating the environmental noise is generated for each of the sites and is stored in the storage unit 410.

In the first modification example, in Step S103 or S105 illustrated in FIG. 3, the determining unit 404 and the environmental noise estimating unit 405 extract the cause estimation table corresponding to the site that is determined by the site determining unit 413, and determine the presence or absence of the environmental noise and estimate the cause of the environmental noise by using the extracted cause estimation table.

According to the first modification example described above, the same effect as that of the first embodiment described above can be obtained, and the environmental noise is estimated from the error detection result, the number of pieces according to the site, the continuousness, and the periodicity, by estimating the cause of the environmental noise with the cause estimation table that is prepared for each of the sites, and thus, the environmental noise can be more accurately estimated.

Note that, in the first modification example described above, it has been described that the site determining unit 413 determines the site from the receiving strength of each of the receiving antennas 3a to 3h, but the site in which the capsule endoscope 2 exists may be determined on the basis of the position of the capsule endoscope 2 that is estimated on the basis of the size of the receiving strength of each of the receiving antennas 3a to 3h, and the information that is stored in the storage unit 410. In addition, the site determining unit 413 may determine the site in which the capsule endoscope 2 exists, from the image corresponding to the image data of an environmental noise determination target.

Second Modification Example of First Embodiment

Figure 10:
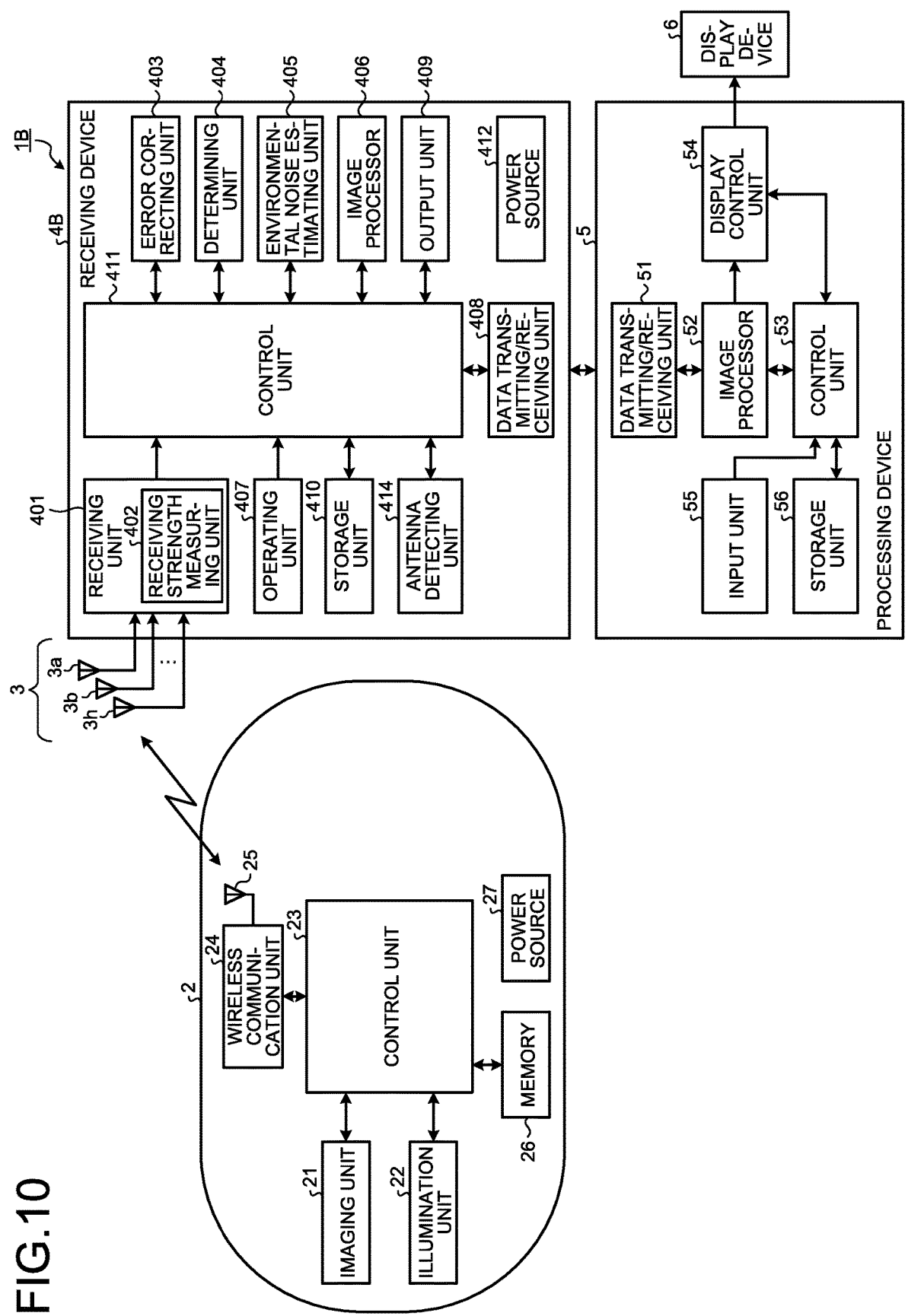
FIG. 10 is a block diagram illustrating a schematic configuration of a capsule endoscope system according to a second modification example of the first embodiment of the disclosure.

Subsequently, a second modification example of the first embodiment of the disclosure will be described. FIG. 10 is a diagram illustrating the configuration of a capsule endoscope provided in a capsule endoscope system according to a second modification example of the first embodiment of the disclosure. A capsule endoscope system 1B according to the second modification example is different from the capsule endoscope system 1 described above in that a receiving device 4B is provided instead of the receiving device 4. The other configurations are identical to those of the capsule endoscope system 1. Hereinafter, a configuration and processing different from that of the first embodiment described above will be described with reference to FIG. 10.

The receiving device 4B further includes an antenna detecting unit 414, in addition to the configuration of the receiving device 4 described above. The antenna detecting unit 414 detects the type of receiving antenna unit 3 that is connected to the receiving device 4B, and outputs a detection result to the control unit 411. The type can be detected by the antenna detecting unit 414 by a known method such as a method of detecting the type from the disposition of a pin that is provided in a connector portion of the connected receiving antenna unit 3. At this time, the cause estimation table for estimating the environmental noise is generated for each of the types, and is stored in the storage unit 410.

In the second modification example, in Step S103 or S105 illustrated in FIG. 3, the determining unit 404 and the environmental noise estimating unit 405 extract the cause estimation table corresponding to the type that is detected by the antenna detecting unit 414, and determine the presence or absence of the environmental noise and estimate the cause of the environmental noise by using the extracted cause estimation table.

According to the second modification example described above, the same effect as that of the first embodiment described above can be obtained, and the environmental noise is estimated from the error detection result, the number of pieces according to the type of receiving antenna unit 3, the continuousness, and the periodicity, by estimating the cause of the environmental noise with the cause estimation table that is prepared for each type of receiving antenna unit 3, and thus, the environmental noise can be more accurately estimated.

Note that, the cause estimation table may be prepared for each body type of subject, and the environmental noise estimating unit 405 may estimate the environmental noise, on the basis of the cause estimation table according to the body type that is input, in addition to the first modification example and the second modification example described above. In addition, the cause estimation table may be changed in accordance with whether or not a shielding member such as a jacket woven with a shield is mounted on the subject, in order to shield the environmental noise.

Second Embodiment

Figure 11:
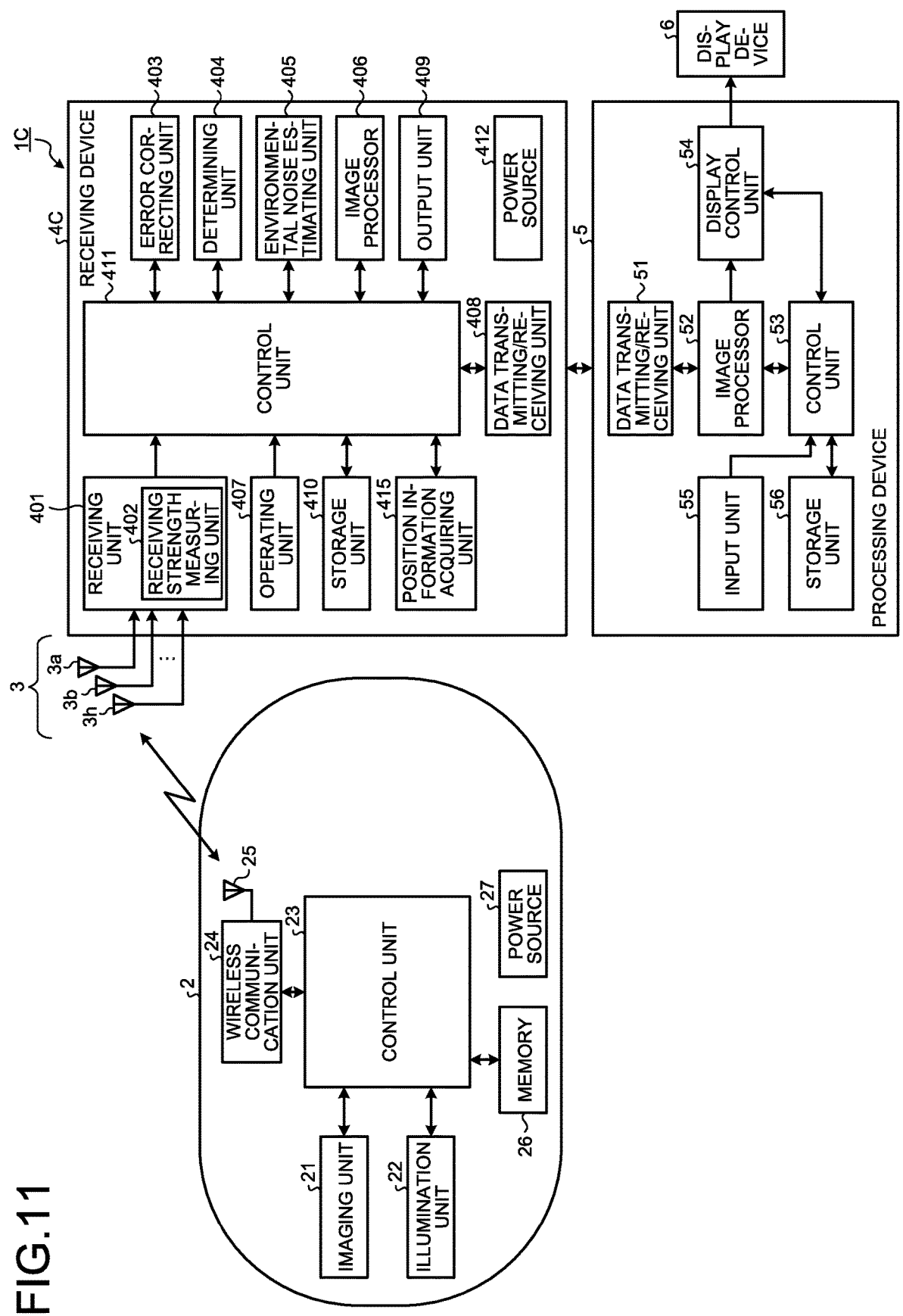
FIG. 11 is a block diagram illustrating a schematic configuration of a capsule endoscope system according to a second embodiment of the disclosure.

Subsequently, a second embodiment of the disclosure will be described. FIG. 11 is a diagram illustrating the configuration of a capsule endoscope provided in a capsule endoscope system according to the second embodiment of the disclosure. A capsule endoscope system 1C according to the second embodiment is different from the capsule endoscope system 1 described above in that a receiving device 4C is provided instead of the receiving device 4. The other configurations are identical to those of the capsule endoscope system 1. Hereinafter, a configuration and processing different from that of the first embodiment described above will be described with reference to FIG. 11.

The receiving device 4C further includes a position information acquiring unit 415, in addition to the configuration of the receiving device 4 described above. The position information acquiring unit 415 is configured by using a global positioning system (GPS) receiver that receives an electric wave from a GPS satellite. The position information acquiring unit 415 performs positioning with respect to a position at the time of receiving the signal, on the basis of the received signal, and outputs a positioning result to the control unit 411, as position information. The positioning of the position information acquiring unit 415 can be performed by using a known method.

In a case where the position information is acquired from the position information acquiring unit 415, the control unit 411 stores the image data that is generated at the time of receiving the signal, the position information, and the information relevant to the environmental noise of the image data, in the storage unit 410, in association with each other.

In the processing device 5, a position in which the environmental noise is generated is mapped on a map, from the position information and the information relevant to the environmental noise, and thus, it is possible to display a map explicitly illustrating a location in which the environmental noise that should be avoided exists, on the display or the like. A medical doctor is capable of displaying such a map, and of instructing the subject into which the capsule endoscope 2 is inserted in the location that should be avoided in order to prevent the environmental noise from being superimposed.

According to the second embodiment described above, the same effect as that of the first embodiment described above can be obtained, and the subject can be instructed in advance to avoid the location that can be affected by the environmental noise, by combining the position information of the GPS and the environmental noise, and by mapping the location in which the environmental noise exists, on the map.

In the second embodiment described above, the position information acquiring unit 415 may further acquire the history of a card reader that is provided in a facility, in addition to the position information of the GPS. The control unit 411 stores the history of the card reader and the information relevant to the environmental noise of the image data in the storage unit 410, in association with each other, in addition to the position information of the GPS. Further, the receiving device 4C maps the position in which the environmental noise is generated, on the map, from the position information of the GPS, the position information including the history of the card reader, and the information relevant to the environmental noise. At this time, it is possible to associate the facility corresponding to the card reader with the information relevant to the environmental noise of the image data corresponding to a time stamped by the card reader, from the history of the card reader. Note that, in the processing device 5, the position in which the environmental noise is generated may be mapped on the map.

Modification Example of Second Embodiment

Figure 12:
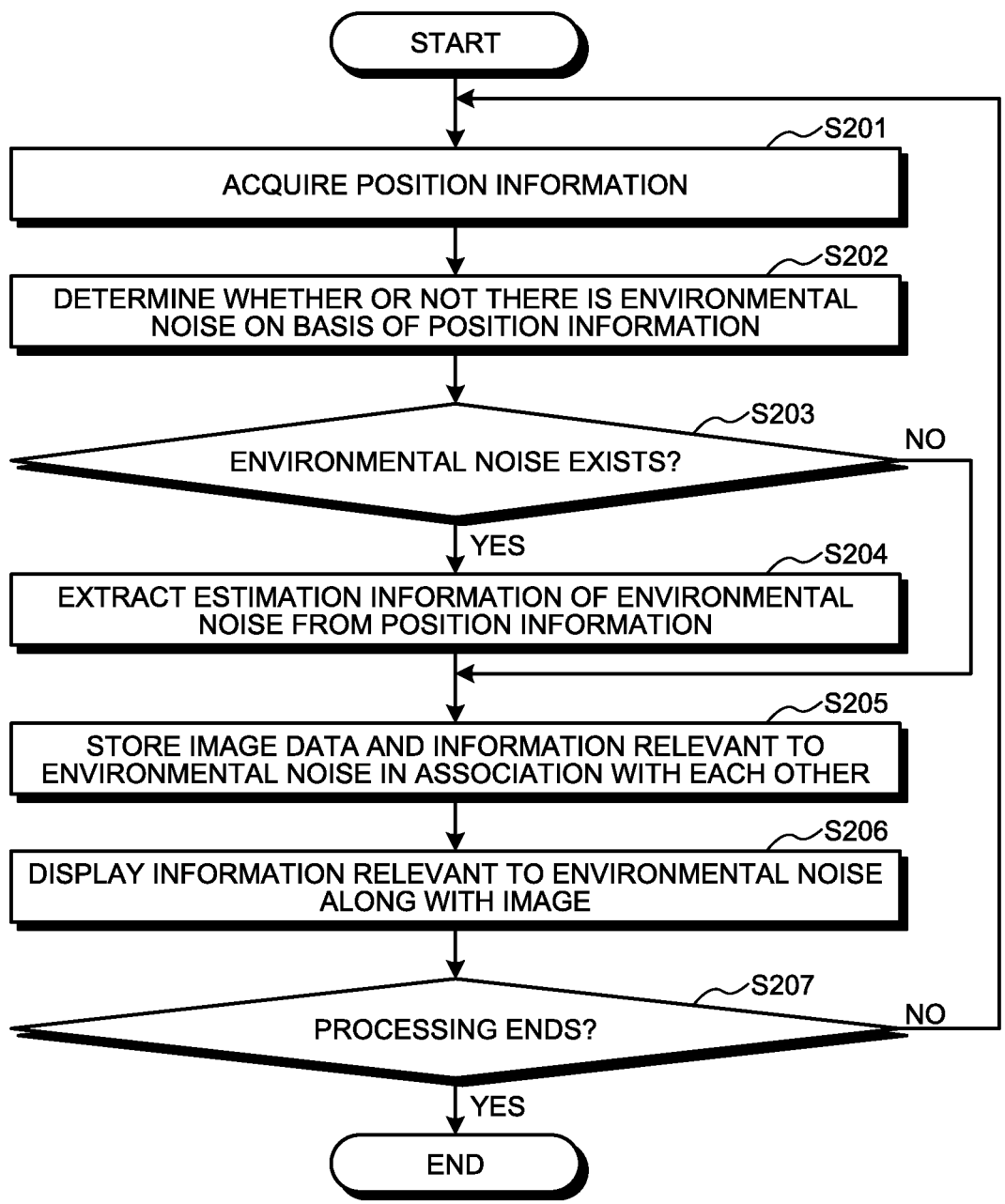
FIG. 12 is a flowchart illustrating environmental noise estimation processing that is performed by a capsule endoscope system according to a modification example of the second embodiment of the disclosure.

Subsequently, a modification example of the second embodiment of the disclosure will be described. FIG. 12 is a flowchart illustrating environmental noise estimation processing that is performed by a capsule endoscope system according to the modification example of the second embodiment of the disclosure. The capsule endoscope system according to the modification example is identical to the capsule endoscope system 1C described above. Hereinafter, processing different from that of the second embodiment described above will be described with reference to FIGS. 12 and 13. Note that, in the modification example, as described above, it is described that map information in which the location that should be avoided in order to prevent the environmental noise from being superimposed is mapped on the map is stored in the storage unit 410.

First, in a case where the position information acquiring unit 415 receives a signal from the GPS satellite, the position is subjected to the positioning from the received signal, and the position information is generated (Step S201).

In Step S202 subsequent to Step S201, the determining unit 404 compares the acquired position information with the map information that is stored in the storage unit 410, and determines whether or not there is the environmental noise in the position that is subjected to the positioning.

In Step S203 subsequent to Step S202, in a case where the determining unit 404 determines that there is the environmental noise (Step S203: Yes), the control unit 411 proceeds to Step S204. In contrast, in a case where the determining unit 404 determines that there is no environmental noise (Step S203: No), the control unit 411 proceeds to Step S205.

In Step S204, the environmental noise estimating unit 405 extracts the environmental noise that is estimated on the basis of the map information, from the position information, and sets the environmental noise as an estimation result. The environmental noise estimating unit 405 generates estimation information relevant to the estimated environmental noise, and outputs the estimation information to the control unit 411.

In Step S205, the control unit 411 associates the image data with the information relevant to the environmental noise, and stores the image data and the information relevant to the environmental noise in the storage unit 410. At this time, in a case where it is determined that there is the environmental noise, the cause of the estimated environmental noise is associated with the image data corresponding to a time when the positioning is performed. In contrast, for example, in a case where it is determined that there is no environmental noise, information to the effect that there is no environmental noise is applied to the image data at the time when the positioning is performed.

Figure 13:
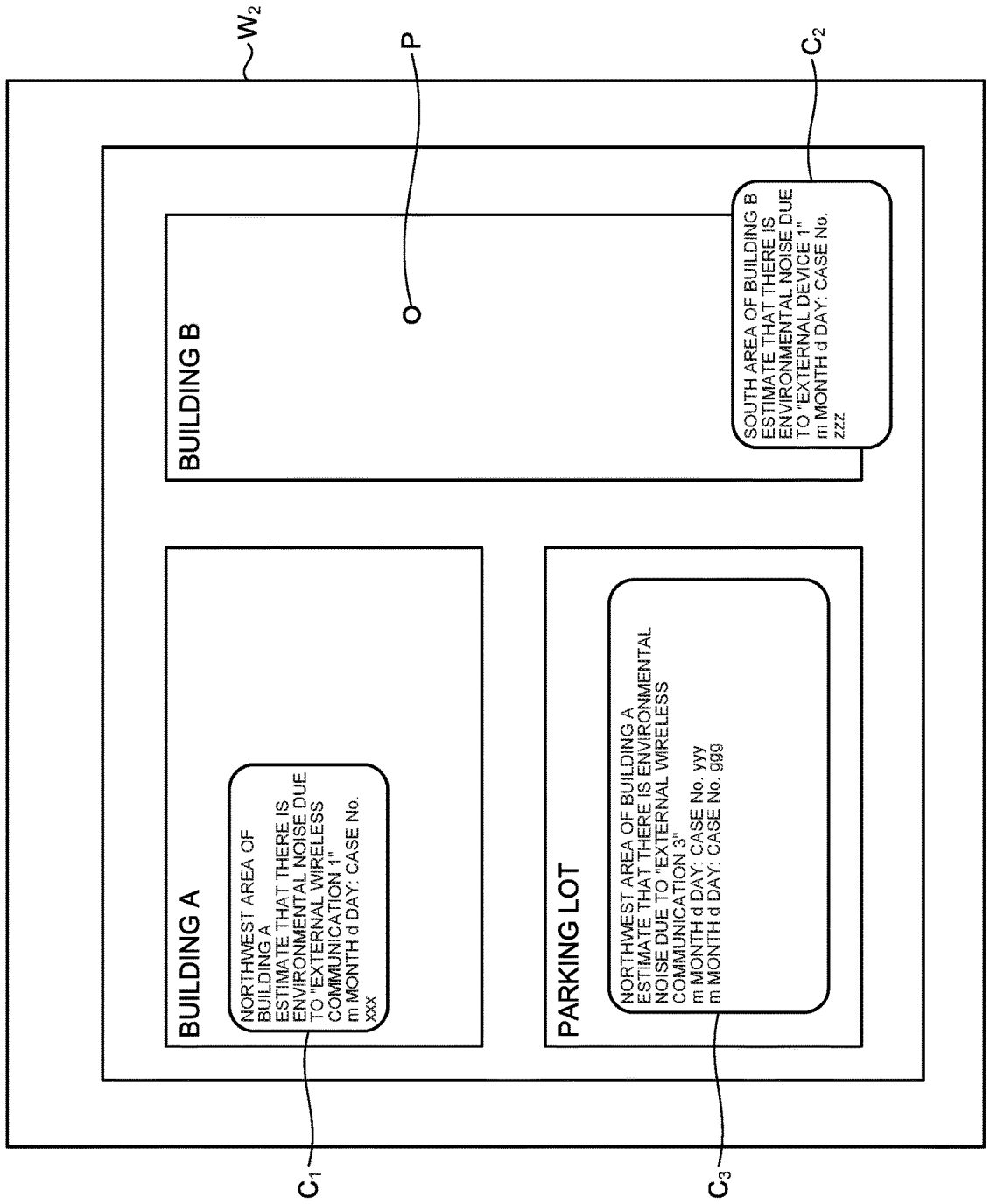
FIG. 13 is a diagram illustrating an example of display of information relevant to an estimated environmental noise, in the capsule endoscope system according to the modification example of the second embodiment of the disclosure.

In Step S206 subsequent to Step S205, the control unit 411 causes the output unit 409 (the display) to display the information relevant to the environmental noise on the output unit 409, along with the image corresponding to the image data. FIG. 13 is a diagram illustrating an example of the display of the information relevant to the estimated environmental noise, in the capsule endoscope system according to the modification example of the second embodiment of the disclosure. In Step S206, for example, as with a screen $W_2$ illustrated in FIG. 13, the image corresponding to the map information, a current location mark P indicating a position in which the positioning is performed, and comments $C_1$ to $C_3$ relevant to the location that should be avoided in each of the facilities are displayed.

When the image is displayed on the display, the output unit 409 emits a sound, and thus, notifies that the image is displayed on the display.

The user mounted with the receiving device 4C checks the image that is displayed on the display (refer to FIG. 13), and thus, it is possible to suppress the noise that is superimposed on the image data by avoiding the environmental noise.

After that, the control unit 411 determines whether or not an instruction to the effect of ending the environmental noise estimation processing is received (Step S207). In a case where the control unit 411 determines that there is no instruction to the effect of ending the environmental noise determination processing (Step S207: No), the control unit 411 returns to Step S201, and the processing described above is repeated with respect to a signal that is newly received. In contrast, in a case where the control unit 411 receives the instruction to the effect of ending the environmental noise estimation processing (Step S207: Yes), the environmental noise estimation processing is ended.

In the modification example described above, the wireless transmission source (the cause) that should be avoided in order to suppress the noise superimposed on the image data can be estimated in real time, from GPS information, and the map information to which the information relevant to the environmental noise is applied, and can be given in notification to the subject.

In addition, the execution program with respect to each of the processings executed by each of the constituents of the capsule endoscope, the receiving device, and the processing device of the capsule endoscope system according to the first embodiment and the second embodiment may be provided by being recorded in a computer readable recording medium such as a CD-ROM, a flexible disk (FD), a CD-R, and a DVD, in a file of an installable format or an executable format, or may be provided by being stored on a computer connected to a network such as the Internet, and by being downloaded through the network. In addition, the execution program may be provided or distributed through the network such as the Internet.

In addition, in the first embodiment and the second embodiment, it has been described that the wireless signal is generated by the capsule endoscope 2 that is the medical device, and is output, but the medical device is not limited to the capsule endoscope 2 insofar as the wireless signal is generated and output. For example, a pacemaker that is capable of being attached to the subject, and is capable of generating and outputting the wireless signal, or the like may be used as the medical device.

As described above, the estimation device, the medical system, the estimation method, and the estimation program according to the disclosure are useful for estimating the wireless transmission source that should be avoided in order to suppress the noise superimposed on the image data.

According to the disclosure, an effect is obtained in which it is possible to estimate a wireless transmission source that should be avoided in order to suppress a noise superimposed on image data.

What is claimed is:

1. An estimation device, comprising
a processor comprising hardware, the processor being configured to:
detect an error of data obtained by receiving a wireless signal from a medical device configured to be inserted into a subject;
correct the detected error;
determine whether or not there is a noise due to an external generation source at a time of acquiring the wireless signal from the medical device, based on detection information relevant to the detected error or correction information relevant to the corrected error; and
estimate a cause of the noise, based on the detection information or the correction information, when it is determined that there is the noise,
wherein the detection information is at least one of the number of detections of the error, continuousness of the error, and periodicity of the error, and
the correction information is at least one of the number of corrections of the error, continuousness of data in which the error is corrected, and periodicity of data in which the error is corrected.

2. The estimation device according to claim 1,
wherein the processor is configured to estimate the cause of the noise, based on the detection information or the correction information, and on information relevant to a candidate of the external generation source.

3. The estimation device according to claim 1,
wherein the processor is configured to estimate the external generation source that is positioned around the subject and that emits an electromagnetic wave having a predetermined frequency band.

4. The estimation device according to claim 1, further comprising:
a controller configured to control the processor to output the cause of the noise, within a predetermined time after the estimation of the cause of the noise has been ended.

5. The estimation device according to claim 4, further comprising:
a position information receiver configured to acquire position information of the estimation device,
wherein the controller is configured to generate information in which the position information and the cause of the noise are associated with each other.

6. The estimation device according to claim 1,
wherein the medical device is a capsule endoscope.

7. A medical system, comprising:
a medical device to be inserted into a subject, the medical device being configured to output a wireless signal;
a receiver configured to receive the wireless signal;
a first processor comprising hardware, the first processor being connected to the receiver to communicate with the receiver; and
a display,
wherein the receiver includes
a second processor comprising hardware, and
a position information receiver configured to acquire position information of the receiver,
the second processor is configured to
detect an error of data obtained by receiving the wireless signal from the medical device,
correct the detected error,
determine whether or not there is a noise due to an external generation source at a time of acquiring the wireless signal from the medical device, based on detection information relevant to the detected error or correction information relevant to the corrected error, and
estimate a cause of the noise, based on the detection information or the correction information, when it is determined that there is the noise,
the detection information is at least one of the number of detections of the error, continuousness of the error, and periodicity of the error,
the correction information is at least one of the number of corrections of the error, continuousness of the data in which the error is corrected, and periodicity of the data in which the error is corrected, and the first processor is configured to cause the display to display information in which the position information and the cause of the noise are associated with each other on the display.

8. The medical system according to claim 7,
wherein the second processor is configured to estimate the external generation source that is positioned around the subject and that emits an electromagnetic wave having a predetermined frequency band.

9. The medical system according to claim 7,
wherein the receiver further includes a controller configured to control the second processor to output the cause of the noise, within a predetermined time after the estimation of the cause of the noise has been ended.

10. The medical system according to claim 9,
wherein the controller is configured to generate the information in which the position information and the cause of the noise are associated with each other.

11. The medical system according to claim 7,
wherein the medical device is a capsule endoscope.

12. An estimation method performed by an estimation device configured to estimate a cause of a noise due to an external generation source, based on data obtained by receiving a wireless signal from a medical device configured to be inserted into a subject, the method comprising:
   detecting an error of the data;
   correcting the detected error;
   determining whether or not there is the noise at a time of acquiring the wireless signal from the medical device, based on detection information relevant to the detected error or correction information relevant to the corrected error; and
   estimating the cause of the noise, based on the detection information or the correction information, when it is determined that there is the noise,
   wherein the detection information is at least one of the number of detections of the error, continuousness of the error, and periodicity of the error, and
   the correction information is at least one of the number of corrections of the error, continuousness of the data in which the error is corrected, and periodicity of the data in which the error is corrected.

13. The estimation method according to claim 12,
wherein the estimating includes estimating the external generation source that is positioned around the subject and that emits an electromagnetic wave having a predetermined frequency band.

14. The estimation method according to claim 12, further comprising:
   controlling the estimation device to output the cause of the noise, within a predetermined time after the estimation of the cause of the noise in the noise estimation step has been ended.

15. The estimation method according to claim 14, further comprising:
   acquiring position information of the estimation device,
   wherein the controlling includes generating information in which the position information and the cause of the noise are associated with each other.

16. The estimation method according to claim 12,
wherein the medical device is a capsule endoscope.

* * * * *